US008367734B1

(12) United States Patent
Gao et al.

(10) Patent No.: US 8,367,734 B1
(45) Date of Patent: Feb. 5, 2013

(54) STABLE EPINEPHRINE SUSPENSION FORMULATION WITH HIGH INHALATION DELIVERY EFFICIENCY

(75) Inventors: Jianxin Gao, Norton, MA (US); James Luo, Quincy, MA (US); Rong Zhou, Fullerton, CA (US); Mary Ziping Luo, Diamond Bar, CA (US); Jack Yongfeng Zhang, Diamond Bar, CA (US)

(73) Assignee: Amphastar Pharmaceuticals Inc., Rancho Cucamonga, CA (US)

( * ) Notice: Subject to any disclaimer, the term of this patent is extended or adjusted under 35 U.S.C. 154(b) by 168 days.

(21) Appl. No.: 12/776,338

(22) Filed: May 7, 2010

Related U.S. Application Data

(63) Continuation-in-part of application No. 11/200,634, filed on Aug. 11, 2005, now abandoned.

(51) Int. Cl.
*A61K 31/135* (2006.01)
*A61K 31/05* (2006.01)
*A61K 9/12* (2006.01)
*A61K 9/14* (2006.01)

(52) U.S. Cl. ............ 514/653; 514/728; 424/45; 424/46; 424/489

(58) Field of Classification Search .................. 514/653, 514/728; 424/45, 46, 489
See application file for complete search history.

(56) References Cited

U.S. PATENT DOCUMENTS

| | | | |
|---|---|---|---|
| 3,014,844 A | 12/1961 | Thiel et al. | |
| 3,219,533 A | 11/1965 | Mullins | |
| 3,322,625 A | 5/1967 | Shimmin | |
| 4,352,789 A | 10/1982 | Thiel | |
| 5,225,183 A | 7/1993 | Purewal et al. | |
| 5,451,401 A * | 9/1995 | Zerby et al. | 424/57 |
| 5,534,242 A | 7/1996 | Henry | |
| 5,560,607 A | 10/1996 | Macroglou | |
| 6,039,932 A | 3/2000 | Govind et al. | |
| 6,054,488 A | 4/2000 | Oliver et al. | |
| 6,086,376 A | 7/2000 | Moussa et al. | |
| 6,126,919 A | 10/2000 | Stefely et al. | |
| 6,129,905 A | 10/2000 | Cutie | |
| 6,416,742 B1 | 7/2002 | Stefely et al. | |
| 6,451,285 B2 | 9/2002 | Blondino et al. | |
| 6,451,289 B2 | 9/2002 | Wherry, III et al. | |
| 6,458,338 B1 | 10/2002 | Adjei et al. | |
| 6,461,591 B1 | 10/2002 | Keller et al. | |
| 6,503,482 B1 | 1/2003 | Fassberg et al. | |
| 6,532,955 B1 | 3/2003 | Ashurst et al. | |
| 6,596,260 B1 | 7/2003 | Brugger et al. | |
| 6,630,129 B2 | 10/2003 | Cripps et al. | |
| 6,638,495 B2 | 10/2003 | Weers et al. | |
| 6,737,044 B1 | 5/2004 | Dickinson et al. | |
| 6,743,413 B1 | 6/2004 | Schultz et al. | |
| 6,776,432 B2 | 8/2004 | Harkcom et al. | |
| 7,459,146 B2 | 12/2008 | Baran, Jr. et al. | |
| 2005/0118310 A1 * | 6/2005 | Lacroix | 426/240 |
| 2006/0162722 A1 * | 7/2006 | Boehm et al. | 128/200.14 |

OTHER PUBLICATIONS

Bonevski et al. "Inhibition of Epinephrine Oxidation in Weak Alkaline Solutions," Journal of Pharmaceutical Sciences, Oct. 1978, 67(10), pp. 1474-1476.*
Connors et al. Chemical Stability of Pharmaceuticals: A Handbook for Pharmacists, 2nd edition, John Wiley & Sons, Inc.: 1986, pp. 445.*
Bowman, Paul A., et al., "Non-CFC metered dose inhalers: the patent landscape," International Journal of Pharmaceuticals, 186, 1999, pp. 91-94.
Byron, Peter R., "Performance Characteristics of Pressurized Metered Dose Inhalers in Vitro," Journal of Aerosol Medicine, 10(1), 1997, pp. S-3-S-7.
Fink, James B., "Metered-Dose Inhalers, Dry Powder Inhalers, and Transitions," Respiratory Care, 45(6), Jun. 2000, pp. 623-635.
Fink, James B., et al., "Reconciling in Vitro and in Vivo Measurements of Aerosol Delivery from a Metered-Dose Inhaler during Mechanical Ventilation and Defining Efficiency-enhancing Factors," American Journal of Respiratory and Critical Care Medicine, 159, 1999, pp. 63-68.
Hirst, Peter H., et al. "In Vivo Lung Deposition of Hollow Porous Particles form a Pressurized Metered Dose Inhaler," Pharmaceutical Research, 19(3), Mar. 2002, pp. 258-264.
Keller, Manfred, "Innovations and perspectives of metered dose inhalers in pulmonary drug delivery," International Journal of Pharmaceutics, 186, 1999, pp. 81-90.
Ramsdell, Joe W., et al., "Cumulative dose response study comparing HFA-134a albuterol sulfate and conventional CFC albuterol in patients with asthma," Annals of Allergy, Asthma, & Immunology, 81, Dec. 1998, pp. 593-599.
Stefely, James S., "Novel Excipients for Inhalation Drug Delivery: Expanding the Capability of the MDI," Drug Delivery Technology, 2(6), Sep. 2002, 11 pages.
Szulczewski, Dale H., et al., "Epinephrine," Analytical Profiles of Drug Substances, Academic Press, Inc., 1978, p. 213.
Vaswani, Surender K., et al., "Metered dose inhaler: past, present, and future," Annals of Allergy, Asthma, & Immunology, 80, Jan. 1998 pp. 11-20, 23.
Williams III, R.O., et al., "A study of an epoxy aerosol can lining exposed to hydrofluoroalkane propellants," European Journal of Pharmaceutics and Biopharmaceutics, 44, 1997, pp. 195-203.

* cited by examiner

*Primary Examiner* — James H. Alstrum-Acevedo

(74) *Attorney, Agent, or Firm* — Christie, Parker & Hale, LLP

(57) ABSTRACT

A stable suspension aerosol formulation of epinephrine is suitable for administration through inhalation comprising a therapeutically effective amount of epinephrine, hydrofluorocarbon propellant, co-solvent, surfactant, and antioxidant. The suspension aerosol formulation further comprises [pre-] pre-micronized epinephrine suspended in an alcohol/surfactant solution with hydrofluoroalkane propellant. The suspension formulation provides a highly efficient delivery of drug microparticles into the respirable region of patients' lungs and has the following advantages: lower dosage requirement, minimum alcohol content, with less impurities generated during storage, improved efficacy and safety, and exhibits no ozone depleting potential compared to a formulation containing chlorofluorocarbon.

13 Claims, 2 Drawing Sheets

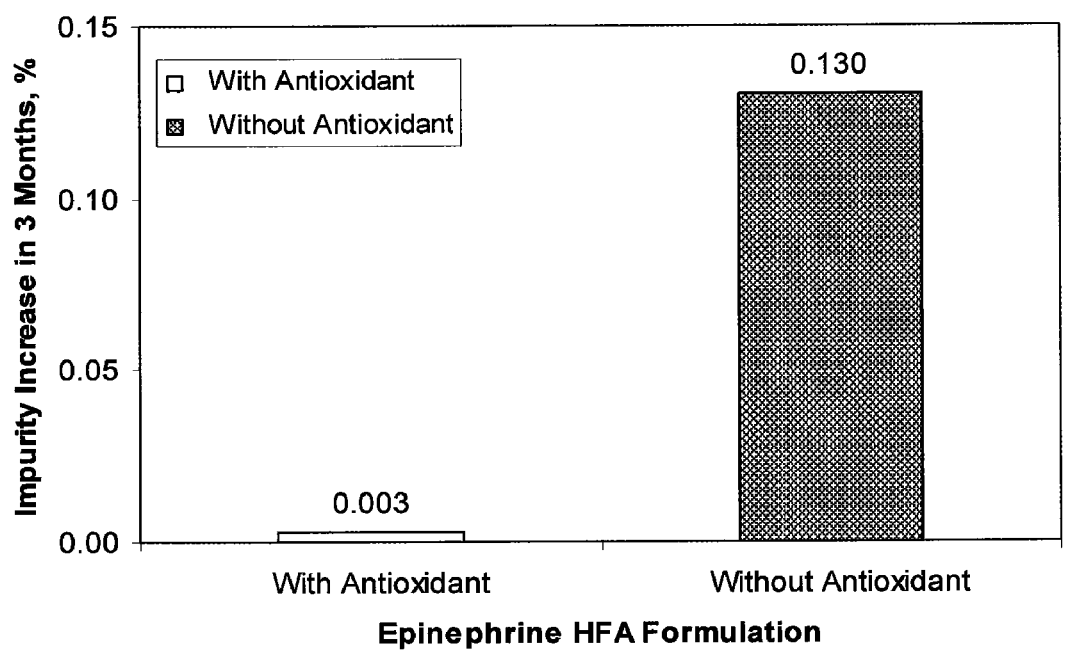
Figure 1 Epinephrine HFA Formulation and Impurity Increase

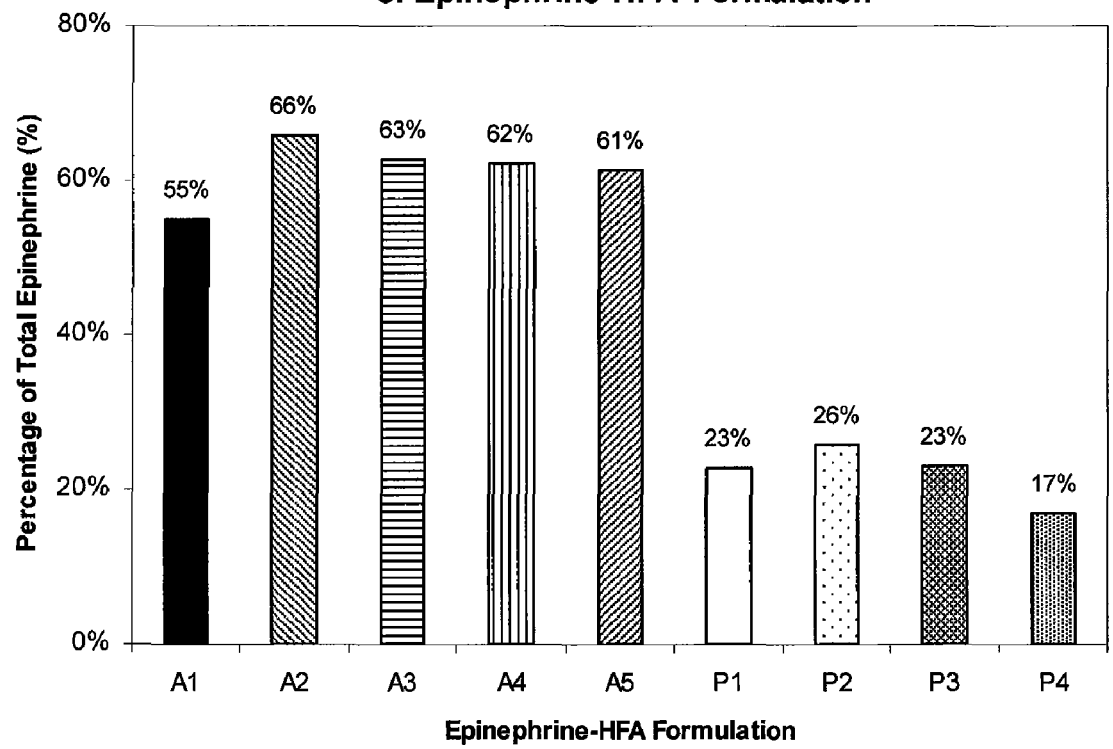

US 8,367,734 B1

STABLE EPINEPHRINE SUSPENSION FORMULATION WITH HIGH INHALATION DELIVERY EFFICIENCY

RELATED APPLICATION

This application is a continuation in part of and claims the benefit of priority to U.S. patent application Ser. No. 11/200,634 filed Aug. 11, 2005 now abandoned entitled "Suspension Formulation Containing Epinephrine and Hydrofluoroalkane Propellant", the disclosure of which is incorporated herein by reference.

TECHNICAL FIELD

The invention generally pertains to aerosol formulations for the delivery of medications suitable for administration via the respiratory tract. More particularly, the present invention pertains to a stable suspension formulation containing epinephrine, or its salt forms, and hydrofluoroalkane propellant for use in a metered dose inhaler, with high inhalation delivery efficiency.

BACKGROUND ART

Medications for the treatment of respiratory disorders are commonly administered by inhalation through the mouth or nose in an aerosol formulation. As with any other delivery method, safety, toxicity and bioavailability, are the main concerns. The inhalation route can provide superior advantages for the treatment of pulmonary diseases, as compared with other means of administration such as oral or injection. Injection is the most effective method of administration to a patient's blood stream, however it is a painful administration procedure, and systemic side effects may occur from the unwarranted spread of drug molecules such as steroids and beta-blockers. While oral intake is the preferred alternative for drug administration, it often requires large doses of the medication in order to be effective, which can result in unwanted side effects. Drug delivery by inhalation can effectively deposit a medication locally at a targeted therapeutic site, thereby providing rapid onset, a lower dosing requirement and decreased incidence of side effects.

One of the most widely used devices to deliver a formulation through the inhalation method for the treatment of pulmonary disorders is a metered dose inhaler (MDI). The MDI is widely used for the delivery of bronchodilator type products for the treatment of respiratory disorders such as Chronic Obstructive Pulmonary Disease (COPD) and asthma. The MDI has gained popularity since its introduction decades ago, mainly because administration is convenient and practical. Additionally, the MDI is easy to use, portable, capable of multiple dose delivery, low cost, provides minimal loss of drug within the device at the time of administration, and is a reliable and efficient method of drug delivery to a targeted area of the patient's lungs.

Prior art metered dose inhaler formulations have historically contained chlorofluorocarbon (CFC) as propellants to deliver doses of medication to a patient's lungs. However, CFCs have been associated with the degradation of the ozone layer. Depletion of the ozone layer causes an increase of UV light exposure, which is responsible for numerous health problems such as increased incidence of skin cancer, premature aging of the skin, cataracts/eye damage and suppression of the immune system. The use of CFC's is being phased out as part of the agreement of the Montreal protocol Exceptions have been made for certain uses that are necessary for health and safety, which include MDIs for pharmaceutical use These types of products will be gradually phased out as substitutes become available.

The phasing out of CFCs has led to a flurry of development activities for alternative means of pulmonary drug delivery without the use of CFC propellants. One previous alternative is the use of nebulizers. A nebulizer is pressurized by an oxygen tank or oil free compressed air source for the purpose of vaporizing a liquid medication into a fine mist that is suitable for delivery via the respiratory tract without the use of CFCs. However, nebulizers are expensive and inconvenient for patients because there are problems with dosing uniformity, and nebulizers require a power supply for operation, are cumbersome and require a longer time for drug delivery. A nebulizer is mainly used in an emergency room or for children and elderly patients who cannot operate an MDI themselves.

Another alternative to CFCs that is gaining popularity is a dry powder inhaler (DPI). A DPI has several advantages as it contains no propellant and is breath activated, thus eliminating the need to synchronize inhalation with actuation. However, DPIs do present formulation challenges for delivering micrograms of drug molecules uniformly from dose to dose. A micronized drug has to be mixed with a coarse carrier substance such as lactose, which can cause airway irritation in some asthmatic patients.

Over the years improvements have been made to the drug delivery systems, such as multidose DPIs and more versatile nebulizers that increase convenience and ease of use to patients. However, the advantages and superiority of a MDI remain unchallenged, which is the reason that MDIs remain as the most popular and widely used inhalation delivery device. Thus, reformulation of CFC based medicinal aerosols using a MDI appears to be the best solution. The phase out of CFCs has made this an urgent matter, which has also turned out to be an opportunity to improve the performance of MDIs.

Hydrofluoroalkane (HFA) propellants have emerged as the best alternative to replace CFC propellants in a MDI for pharmaceutical uses. HFA-134a with chemical formula 1,1,1,2-tetrafluoroethane, and HFA-227 with chemical formula 1,1,1,2,3,3,3-heptafluoropropane are considered the most suitable alternative propellants. The development of a new formulation utilizing HFA has proven to be a difficult challenge because this propellant tends not to function with CFC compatible excipients due to differences in the chemical and physical properties of these two propellants. Thus, there is a necessity to develop a new formulation that provides an effective MDI formulation utilizing HFA propellant.

Epinephrine is commonly used as a bronchodilator in the treatment of acute bronchial asthma. Currently, inhalable Epinephrine is only available in CFC form under the name Primatene® manufactured by Armstrong Pharmaceuticals, Inc. Primatene® is a CFC/alcohol solution of epinephrine. It is supplied with a glass bottle because of its low pH due to hydrochloric acid and nitric acid in the CFC formulation. Historically, CFC based MDI formulations with Epinephrine have a problem of low respirable fractions or drug delivery efficiency, and high throat deposition requiring large drug doses to obtain therapeutic efficacy. In addition, epinephrine formulation is easily oxidized which can cause the formulation to become unstable. According to Analytical Profiles of Drug Substances, Vol. 7, p. 213, "Since epinephrine is an o-diphenol containing a hydroxyl group in the $\alpha$ position, it is a strong reducing agent. As such, it is easily oxidized by such oxidizing agents as molecular oxygen. Oxidation of epinephrine by molecular oxygen can also result in formulation of a brownish insoluble material of indefinite structure."

Applicants have now discovered a new epinephrine suspension formulation with improved formulation characteristics that solves prior art problems by eliminating the use of CFCs and adding an antioxidant to produce a stable formulation that exhibits a significantly higher drug deposition in the respirable region of a patient's lungs.

A search of the prior art reveals numerous patents for the preparation of MDI formulations that contain no CFC propellant or contain HFA propellant. However, none of the prior art patents possess the novelty of the instant invention, which introduces a high efficiency stable MDI suspension formulation containing epinephrine or its salt forms with HFA as the propellant for the treatment of asthma, COPD and other respiratory disorders.

SUMMARY OF THE INVENTION

The present invention discloses a high efficiency aerosol suspension formulation that is suitable for administration by inhalation utilizing a metered dose inhaler (MDI). The formulation comprises a therapeutically effective amount of epinephrine or its salt form for the treatment of acute bronchial asthma, chronic obstructive pulmonary diseases and other respiratory disorders. The medication is provided in a suspension formulation that is suitable for delivery in a MDI and essentially consists of micronized epinephrine particles suspended in a low concentration of surfactant and co-solvent solution in hydrofluoroalkane propellant.

The UFA propellant typically consists of 1,1,1,2-tetrafluoroethane (HFA-134a), 1,1,1,2,3,3,3-heptafluoropropane (HFA-227), or a mixture of the two. The preferred surfactants are sorbitan oleates and the preferred co-solvent is ethanol, both of which are present in an amount sufficient to prevent agglomeration or flocculation of the drug particles and to maintain the physical stability of the suspension. A small amount of antioxidant is added to the formulation to minimize impurity generation through oxidation of epinephrine and to ensure the stability of the formulation during storage and use by patients.

The formulation of the present invention provides the following advantages compared to the prior art epinephrine formulation:

(1) the Proposed Epinephrine HFA suspension formulation contains no CFC propellant so that it fulfills the requirements of the Montreal protocol for environmental protection;

(2) the proposed HFA formulation eliminates the need for hydrochloric acid and nitric acid in the CFC formulation, which allows a metal container to be used, thus, eliminating any possibility of broken or even explosive events due to the glass container and is therefore safer for patients;

(3) the proposed HFA formulation has a significantly reduced amount of alcohol which minimizes leaching alcohol-soluble toxic material from the inhalation valves, and will significantly reduce the risk that a patient exhibits a false positive blood alcohol test which may occur if the patient just utilized the current epinephrine inhalation with a high percentage of alcohol and happens to be subjected to a breath alcohol analyzer;

(4) the proposed epinephrine HFA formulation significantly (39 times) reduces the impurities generated due to oxidation of epinephrine during storage and usage by patients, which provides a basis for the drug to meet storage requirement of good manufacturing practice (GMP), and also reduces any risks of adverse events caused by a higher level of impurities;

(5) the proposed epinephrine HFA formulation substantially improves drug delivery to the targeted therapeutic area of the lung, and thus requires a lower dose to produce similar efficacy, which will in turn, reduce the possibility of adverse events of patients caused by a higher dose.

(6) For this proposed epinephrine HFA formulation, the particle size distribution of epinephrine is pre-determined by using pre-micronized epinephrine so that the particle size is well-controlled and its quality is stable and reliable per the requirements of GMP.

In view of the above disclosure, the primary object of the invention is to provide a stable inhalable epinephrine suspension formulation that is capable of efficiently delivering drug molecules to a therapeutic site with improved efficacy and safety.

Another object of the invention is to provide a suspension formulation containing epinephrine and HFA propellant that is suitable for delivery in an MDI and that exhibits a uniform dosing level reproducible over the life of the inhaler.

It is also an object of the invention to provide an inhalable epinephrine suspension aerosol formulation for delivery to the pulmonary air passages that is free of CFC propellant with no ozone depletion potential.

These and other objects and advantages of the present invention will become apparent from the subsequent detailed description of the preferred embodiment and the appended claims.

BRIEF DESCRIPTION OF THE FIGURES

FIG. 1 is a chart showing the impurity level for epinephrine formulations with and without antioxidant after three (3) months storage.

FIG. 2 is a chart showing a comparison of respirable delivery of various inhalable epinephrine formulations.

BEST MODE FOR CARRYING OUT THE INVENTION

The best mode for carrying out the invention is presented in terms of a preferred embodiment for a therapeutically effective amount of drug particles in a suspension aerosol formulation suitable for inhalation delivery using an MDI that is free of CFC. The aerosol formulation is presented in the form of a suspension comprising micronized epinephrine particles suspended in a low concentration of alcohol-surfactant solution with HFA propellant suitable for administration by inhalation. The epinephrine particles in the formulation are pre-micronized to achieve a pre-determined particle size distribution. The formulation is indicated for the treatment of asthma, chronic obstructive pulmonary disease and other respiratory disorders. The suspension formulation of the present invention provides a highly efficient delivery of medication to the therapeutic region of the lungs, and the formulation of the medication is more stable and has less impurities than the product currently marketed.

The preferred medicament in the formulation of the present invention is epinephrine free base in an amount effective to exert the intended therapeutic action through delivery of one or more metered volumes of the formulation. The amount of micronized epinephrine in the formulation ranges from 0.10% to 0.50% w/w relative to the total weight of the formulation.

The formulation of the present invention further comprises a HFA propellant as the energy source to deliver the drug molecules to the lung. The HFA propellant can be selected from the group consisting of 1,1,1,2-tetrafluoroethane, which is also known as HFA-134a, and 1,1,1,2,3,3,3-heptafluoropropane, which is also known as HFA-227, or a mixture thereof. The preferred hydrofluoroalkane propellant is HFA-134a in an amount ranging from 98% to 99% w/w relative to the total weight of the aerosol formulation.

A co-solvent is added into the formulation of the present invention to help solubilize the surfactant and to improve the dispersion characteristics of the micronized epinephrine particles. The co-solvent utilized in the formulation can be selected from the group consisting of ethyl alcohol, isopropyl alcohol, propylene glycol, ethylene glycol, propane, butane, isobutane, pentane, dimethyl ether, diethyl ether and the like. Preferably, the co-solvent selected is ethanol. The ethanol is present in the formulation in an amount ranging from 0.5% to 1.5% w/w of the total weight of the formulation. This amount is substantially less compared to the prior art epinephrine formulation from the current CFC formulation Primatene®, and the epinephrine HFA solution formulation (application Ser. No. 11/052,734) which contains 34%, and 20%-30% alcohol respectively. The low amount of co-solvent provides a significant advantage because a high percentage of ethanol has a negative effect on drug delivery efficiency by increasing the droplet sizes of the formulation during delivery. Thus, it is essential to have only a minimum amount of alcohol in the formulation to produce the fine particle mists that are able to reach the therapeutic region of the lungs upon delivery. The low amount of alcohol provides an additional advantage as it minimizes container component leaching, which reduces the amount of potentially toxic compounds (extractables) leached from the inhaler valve and, gasket into the formulation.

The epinephrine suspension formulation disclosed in the present invention is neutral and allows the use of a metal container and valve to eliminate any potential unsafe events, such as broken glass or even explosive containers, and also provides cost reduction and ease of manufacture.

A small amount of surfactant, preferably less than 0.05 w/w of the total weight of the formulation, is added to provide improved solution properties. The surfactant can be selected from the group consisting of oleic acid, lecithin and sorbitan oleates, e.g., sorbitan mono-oleate and sorbitan trioleate. The preferred surfactant is a sorbitan oleate such as polysorbate 80. The surfactant is included in the formulation to improve the physical stability of the formulation and ensure consistent delivery of medication from the MDI by coating the microparticles, which, in turn, prevents agglomeration of the particles, prevents adhesion of the particles to container walls, and provides lubrication for valve components in the MDI.

A small amount of antioxidant, preferably less than 0.05% w/w of the total weight of the formulation, is also added to the formulation. Epinephrine is one product that is readily oxidized. Thus, the presence of an antioxidant in the formulation is critical to prevent oxidation and maintain stability of the medication to produce a highly efficient epinephrine formulation. Certain antioxidants that are not readily soluble in the formulation might not be appropriate to be used in the present application. The antioxidant that can be used in the present formulation can be selected from the group consisting of thymol, tocopherol, ascorbyl palmitate, butylated hydroxyanisole, butylated hydroxytoluene, propyl gallate, sodium metabisulfite, citric acid, and sodium sulfite. The preferred antioxidant is Thymol.

Table 1 and FIG. 1 shows the impurity profiles of the present epinephrine HFA formulation with and without the antioxidant thymol. As shown in Table 1, the total impurities after three (3) months of storage at 40° C. for the epinephrine formulation with and without thymol increases 11% and 433%, respectively, compared to the total impurities level of the same formulations at zero-time. These data represent that the epinephrine formulation with antioxidant can reduce the total impurities 39 times compared to the formulation without an antioxidant. The high level of impurities during long-term storage in the formulation without the antioxidant thymol can cause the formulation to become unstable, fall out of specification, and make the formulation practically not usable.

TABLE 1

Impurity Profiles of Epinephrine/HFA Formulation with and without Thymol

| | | | | Impurities, as Percentage of the Epinephrine Peak | | | | | Relative Changes of |
|---|---|---|---|---|---|---|---|---|---|
| Formulation | Lot No. | Potency mcg/inh | Time | Impurity #1 [b)] | Impurity #2 [c)] | Impurity #3 [d)] | Total Impurities | Δ of Total Impurities | Total Impurities |
| A1 with Thymol | 0800208 | 60 | Zero-Time | 0.030 | 0.000 | 0.000 | 0.030 | — | — |
| | | | 3 Months [a)] | 0.033 | 0.000 | 0.000 | 0.033 | 0.003 | 11% |
| A1 Without Thymol | 0800608 | 60 | Zero-Time | 0.030 | 0.000 | 0.000 | 0.030 | — | — |
| | | | 3 Months [a)] | 0.043 | 0.030 | 0.087 | 0.160 | 0.130 | 433% |

[a)] Storage conditions: 40 C., 75% Relative humidity.
[b)] Impurity-1: Epinephrine Sulfonic Acid, relative retention time 0.6 minutes;
[c)] Impurity-2: Unknown, relative retention time 2.4 minutes;
[d)] Impurity-3: Unknown, relative retention time 4.2 minutes.

The therapeutic efficacy of an aerosol formulation is determined by the amount of drug particles that are able to penetrate into a patient's deeper lung region. Fine particle fraction (FPF) is a measure of the percentage of drug molecules leaving the MDI that is deposited in the respirable regions of a patient's lungs. A higher fine particle fraction indicates improved delivery efficiency due to a significant decrease in throat deposition. Having a higher fine particle fraction allows a lower amount of total drug dose needed to achieve equivalent therapeutic benefits. Applicants have discovered that the suspension formulation of the present invention is capable of producing a significantly higher fine particle fraction compared to the prior art formulations by suspending the pre-micronized drug particles in the propellant. The suspension formulation can be formulated with a lower amount of drug concentration and only requires a small amount of co-solvent because solubility of epinephrine is not necessary.

Most conventional solution formulations require a higher amount of ethanol to help solubilize the drug molecules. The high amount alcohol will generate a significant number of larger particle droplets and reduce pulmonary delivery efficiency. The suspension formulation of the present invention contains pre-micronized epinephrine microparticles with average particle size smaller than 10 μm, preferably 99% in weight has a particle size less than 5 μm, which permits inhalation of a substantially high percentage of the drug into a patient's lungs upon administration. The small droplet/particle size will lead to less accumulation of the drug in the patient's throat and improve deposition in the alveolar region of the lung.

The preferred formulation of the current invention comprises of pre-micronized epinephrine, with particle sizes less than 5 μm, in an amount ranging from 0.10% to 0.50% w/w, ethanol in an amount ranging from 0.5% to 1.5% w/w, HFA-134a propellant in an amount of 98% to 99% w/w, Polysorbate 80 in an amount less than 0.05% w/w, and Thymol in an amount less than 0.05% w/w. All of the weights disclosed are based on the total weight of the formulation. The suspension formulation is able to produce a significantly higher fine particle fraction compared with the prior art formulations which allows more efficient delivery. This is achieved by suspending the drug microparticles in a surfactant-alcoholic solution in hydrofluoroalkane propellant with the addition of a small amount of an antioxidant, which creates a more uniform dispersion, less agglomeration or sedimentation of the particles, improved stability and efficacy of the formulation.

Table 2 provides a comparison between five (5) proposed formulations with different dosage strength of the Epinephrine HFA suspension formulation and four (4) prior art HFA formulations. Notice that the formulation of the present invention contains a significantly lower amount of alcohol and includes the addition of an antioxidant and exhibits a significantly higher delivery efficiency.

An Andersen cascade impaction analysis coupled with a HPLC assay per USP <601>, Aerodynamic Size Distribution, was used to analyze the fine particle fractions at different stages of the lung. An Andersen cascade impactor has nine stages simulating the various parts of the human respiratory system (the different regions of the lung). The nine stage cascade impactor utilizes jet stages, which enable classification of aerosols from 9.0 micrometers (stage 0) to 0.4 micrometers (stage 7) at 28.3 lpm, and allows drug particles to impact upon stainless steel or aluminum impaction plates. A filter located after the last stage collects all particles smaller than 0.4 micrometers.

TABLE 2

Respirable Delivery Assessment of Epinephrine Inhalation Formulations

| Type of Formulation | | This Application | | | | | Prior Art | | | |
| --- | --- | --- | --- | --- | --- | --- | --- | --- | --- | --- |
| Lot No/Reference No | | 0800208 | 0800909 | 0801209 | 0801009 | 0801109 | 11/052,734 | 11/052,734 | 11/052,734 | EB062409 |
| Symbol of Formulation | | A1 | A2 | A3 | A4 | A5 | P1 | P2 | P3 | P4 |
| Formulation | Epinephrine Bitartrate, % | — | — | — | — | — | — | — | — | 0.3 |
| | Epinephrine, % | 0.12 | 0.19 | 0.27 | 0.35 | 0.48 | 0.29 | 0.27 | 0.24 | — |
| | HFA 134a, % | 42.98 | 98.78 | 98.70 | 98.62 | 98.49 | 74.36 | 75.38 | 77.41 | — |
| | HFA 227, % | 55.87 | — | — | — | — | — | — | — | 91.28 |
| | Ethanol, % | 1.00 | 1.00 | 1.00 | 1.00 | 1.00 | 23 | 22 | 20 | 8.4 |
| | Oleic acid, % | 0.015 | — | — | — | — | — | — | — | 0.02 |
| | Polysorbate 80, % | — | 0.02 | 0.02 | 0.02 | 0.02 | — | — | — | — |
| | Thymol NF, % | 0.01 | 0.01 | 0.01 | 0.01 | 0.01 | — | — | — | — |
| | Ascorbic Acid, % | — | — | — | — | — | 0.07 | 0.07 | 0.07 | — |
| | HCl, % | — | — | — | — | — | 0.82 | 0.76 | 0.68 | — |
| | Purified Water, % | — | — | — | — | — | 1.46 | 1.52 | 1.6 | — |
| | Total, % | 100.00 | 100.00 | 100.00 | 100.00 | 100.00 | 100.00 | 100.00 | 100.00 | 100.00 |
| Cascade Impactor Data | Ad/IP/H * | 23.7 | 26.9 | 40.0 | 54.5 | 71.6 | 75.5 | 72.0 | 59.1 | 68.7 |
| | Stage 0 | 0.5 | 0.4 | 0.8 | 1.07 | 1.62 | 4.8 | 4.6 | 2.9 | 2.3 |
| | Stage 1 | 0.5 | 0.6 | 1.3 | 1.7 | 3.2 | 1.3 | 1.5 | 0.8 | 1.3 |
| | Stage 2 | 0.9 | 1.1 | 2.6 | 4.1 | 6.7 | 0.8 | 0.8 | 0.5 | 2.8 |
| | Stage 3 | 4.1 | 5.9 | 12.4 | 19.9 | 28.9 | 4.0 | 3.8 | 2.5 | 7.5 |
| | Stage 4 | 11.0 | 20.6 | 29.6 | 39.4 | 54.5 | 8.2 | 8.5 | 6.3 | 5.1 |
| | Stage 5 | 15.0 | 28.1 | 32.4 | 40.5 | 46.2 | 9.2 | 11.0 | 7.5 | 2.0 |
| | Stage 6 | 1.5 | 3.6 | 3.3 | 3.8 | 5.5 | 3.0 | 3.5 | 3.1 | 0.6 |
| | Stage 7 | 0.4 | 0.7 | 0.7 | 0.8 | 1.0 | 1.2 | 1.4 | 1.3 | 0.3 |
| | Stage F | 0.7 | 1.6 | 1.6 | 2.3 | 2.6 | 4.0 | 1.7 | 6.3 | 1.2 |
| Total | Total, mcg | 58.2 | 89.4 | 124.8 | 168.1 | 221.8 | 112.0 | 108.8 | 90.3 | 91.9 |
| Respirable Delivery | S3-S7, mcg | 32.0 | 58.8 | 78.4 | 104.5 | 136.1 | 25.6 | 28.2 | 20.7 | 15.6 |
| | S3-S7, % | 55% | 66% | 63% | 62% | 61% | 23% | 26% | 23% | 17% |
| Statistical Analysis for Respirable Delivery | Average ± SD | | | 61% ± 4.0% | | | | 22% ± 3.8% | | |
| | p-value | | | | | 0.000001 | | | | |

* Ad/IP/H : Adapter/Induction port/Head cone.

The drug particle analysis can be separated into three categories:
Drug deposited in the mouth or throat, which is indicated by Ad/IP/H area in the impactor;
Drug that penetrates through the throat but collect in the upper airways due to their relatively large particle size, which is represented by stage 0 to stage 2 in the impactor;
Drug with small particle size that is able to reach the respirable regions of the lung or the effective therapeutic regions, which is represented by stage 3 to stage 7 in the impactor.

Table 2 summarizes the results from the Andersen impaction analysis showing the deposition at different stages of the lung and provides side-by-side comparison between the current HFA suspension formulations with the prior art HFA formulation.

As shown in Table 2, the Epinephrine HFA suspension formulation is capable of delivering significantly higher drug concentration to the respirable region (Stage 3-7) of the instrument, which represents the percentage of drug particles that are capable to deposit in the respirable region of the lungs.

Table 2 reveals that the proposed HFA suspension formulation can deliver up to 2.8 times, fine particle fraction (FPF) in Stage 3-7, compared to the prior art HFA formulations. This occurrence is mainly due to the minimum co-solvent concentration and pre-determined particle size distribution in the present HFA suspension formulation, which allows more drug particles to be delivered and to penetrate deeper into the therapeutic region of the lungs. The results from Andersen cascade impactor analysis can be seen more clearly in FIG. 2, which shows respirable delivery of the different epinephrine formulations.

FIG. 2 clearly illustrates that the present epinephrine suspension formulations, A1-A5, have an obviously higher percentage of medication that reach the respirable region of the lungs compared to the prior art HFA based epinephrine formulations, P1-P4. The mean percentages of respirable delivery of epinephrine are 61%±4.0% and 22%±3.8%, respectively, for this applied formulation and the prior art formulations.

A one-sided t-test for the following hypotheses $$Ho\ X_A \leqq X_P$$

$$Ha\ X_A > X_P$$

where $X_A$ and $X_P$ are pulmonary deliverable fine particle fraction of this applied epinephrine formulation and the prior art epinephrine formulation. The t-test for the above hypotheses obtained a p-value of 0.000001, which is much smaller than 0.05. Thus, the above null hypothesis Ho is rejected, and the alternative hypothesis Ha is accepted. Therefore, the applied epinephrine suspension formulation can deliver significantly more respirable epinephrine than the prior art formulation.

A summary of comparison of the applied epinephrine suspension formulation and the prior art formulation is provided in Table 3.

TABLE 3

Comparison of Applied Epinephrine Formulation with the Prior Art

| # | Formulation | This Application | Prior Art (Appl. No 11/052,734) | Note |
|---|---|---|---|---|
| 1 | Type of Formulation | Suspension | True Solution | |
| 2 | Epinephrine Used | Pre-micronized | — | |
| 3 | Status of Epinephrine in Formulation | Solid particles | Solute, Dissolved | |
| 4 | with antioxidant? | Yes | No | |
| 5 | Increase of Total Impurities after 3-month storage at 40 C. | 0.003% | 0.130% | 1:39 |
| 6 | Pulmonary Delivery Efficiency of Epinephrine (%) | 61% | 22% | 2.8:1 |

The examples and experiment provided are solely for illustration purposes and not meant to limit the invention in any way. While the invention has been described in complete detail, it is not to be limited to such details, since many changes and modifications may be made to the invention without departing from the spirit and scope thereof. Hence, it is described to cover any and all modifications and forms, which may come within the language and scope of the appended claims.

The invention claimed is:

1. An aerosol formulation for use with a metered dose inhaler comprising:

a. a suspension dosage form of pre-micronized epinephrine free base, b. a pressure liquefied propellant comprising a hydrofluoroalkane present in an amount in a range of 98% or more w/w based on the total weight of the formulation, c. a co-solvent selected from the group consisting of ethyl alcohol, isopropyl alcohol, propylene glycol, ethylene glycol, propane, butane, isobutene, pentane, dimethyl ether, and diethyl ether, the co-solvent being present in the aerosol formulation and the amount of the co-solvent being less than 2% w/w based on the total weight of the formulation, d. a surfactant selected from the group consisting of mono- or poly-sorbitan oleates, oleic acid, and lecithin, and e. an antioxidant selected from the group consisting of thymol, tocopherol, ascorbyl palmitate, butylated hydroxyanisole, butylated hydroxytoluene, propyl gallate, citric acid, sodium metabisulfite and sodium sulfite, the antioxidant being present in the formulation.

2. The aerosol formulation as specified in claim 1, wherein said pre-micronized epinephrine free base is present in an amount in a range of 0.10% to 0.50% w/w based on the total weight of the formulation.

3. The aerosol formulation as specified in claim 1, wherein 99% in weight of said pre-micronized epinephrine free base has a particle size in a range of less than 5 micrometers in diameter.

4. The aerosol formulation as specified in claim 1, wherein said liquefied propellant comprises a hydrofluoroalkane selected from the group consisting of 1,1,1,2-tetrafluoroethane (HFA-134A), 1,1,1,2,3,3,3-heptafluoropropane (HFA-227), or a mixture thereof in an amount in a range of 98% or more w/w based on the total weight of the formulation.

5. The aerosol formulation as specified in claim 1, wherein said co-solvent is ethanol in an amount in a range of 0.5% to 1.5% w/w based on the total weight of the formulation.

6. The aerosol formulation as specified in claim 1, wherein said surfactant is present in an amount of no more than 0.05% w/w based on the total weight of the formulation.

7. The aerosol formulation as specified in claim 1, wherein said antioxidant is present in an amount of no more than 0.05% w/w based on the total weight of the formulation.

8. The aerosol formulation as specified in claim 1, wherein said formulation has a fine particle fraction which improves drug delivery efficiency and allows for a lower amount of total drug dosage to achieve therapeutic benefits as compared to a formulation containing less than 98% hydrofluoroalkane.

9. An aerosol formulation for use with a metered dose inhaler comprising:

a. pre-micronized epinephrine free base suspended in a surfactant-alcoholic solution in an amount in a range of 0.1% to 0.50% w/w based on the total weight of the formulation;

b. hydrofluoroalkane propellant in an amount in a range of 98% or more w/w of the total weight of the formulation;

c. an alcohol in an amount in a range of 0.5% to 1.5% w/w based on the total weight of the formulation;

d. polysorbate in an amount of no more than 0.05% w/w based on the total weight of the formulation; and e. thymol in an amount of no more than 0.05% w/w based on the total weight of the formulation, the thymol being present in the formulation, wherein 99% in weight of said pre-micronized epinephrine free base has a particle size of less than 5 micrometers in diameter.

10. An aerosol formulation for use with a metered dose inhaler comprising:
- a suspension dosage form of pre-micronized epinephrine free base;
- a pressure liquefied propellant comprising a hydrofluoroalkane present in an amount in a range of 98% or more w/w based on the total weight of the formulation;
- a co-solvent selected from the group consisting of ethyl alcohol, isopropyl alcohol, propylene glycol, ethylene glycol, propane, butane, isobutane, pentane, dimethyl ether, diethyl ether and mixtures thereof, the co-solvent being present in the aerosol formulation and the amount of the co-solvent being less than 2% w/w based on the total weight of the formulation; and
- a surfactant.

11. The aerosol formulation as specified in claim 10, wherein the co-solvent is present in an amount in a range of 1% to less than 2% w/w based on the total weight of the formulation.

12. The aerosol formulation as specified in claim 10, wherein the co-solvent is present in an amount less than or equal to 1% w/w based on the total weight of the formulation.

13. The aerosol formulation as specified in claim 10, wherein the hydrofluoroalkane is present in an amount of 98% to 99% w/w based on the total weight of the formulation.

* * * * *